US00PP12711P2

(12) United States Plant Patent
Herrera

(10) Patent No.: US PP12,711 P2
(45) Date of Patent: Jun. 18, 2002

(54) CHRYSANTHEMUM PLANT NAMED 'DUSTY PINK SUERTE'

(75) Inventor: Camilo Herrera, Bogota (CO)

(73) Assignee: Interamericana de Asistencia Technica, Panama City (PN)

( * ) Notice: Subject to any disclaimer, the term of this patent is extended or adjusted under 35 U.S.C. 154(b) by 4 days.

(21) Appl. No.: 09/756,357

(22) Filed: Jan. 9, 2001

(51) Int. Cl.[7] ..... A01H 5/00
(52) U.S. Cl. ..... Plt./297
(58) Field of Search ..... Plt./297

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Dusty Pink Suerte', characterized by its daisy-type inflorescences that are about 7.7 cm in diameter; attractive soft pink ray and bright yellow disc florets; very freely flowering habit with numerous inflorescences per stem; response time about 67 days; dark green foliage; strong stems; long peduncles; and good postproduction longevity with inflorescences maintaining good substance and color for at least four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Dusty Pink Suerte'.

The new Chrysanthemum was discovered by the Inventor in a controlled environment in Madrid, Cundinamarca, Columbia in June, 1998, as a naturally-occurring mutation of the *Chrysanthemum×morifolium* cultivar Suerte, disclosed in U.S. Plant Pat. No. 10,225. The new Chrysanthemum was observed as a single plant in a group of flowering plants of the parent cultivar. The selection of this plant was based on its different ray floret color.

Asexual reproduction of the new Chrysanthemum by terminal cuttings taken in a controlled environment in Madrid, Cundinamarca, Colombia, has shown that the unique features of this new Chrysanthemum are stable and reproducted true to type in successive generations.

SUMMARY OF THE INVENTION

The cultivar Dusty Pink Suerte has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dusty Pink Suerte'. These characteristics in combination distinguish 'Dusty Pink Suerte' as a new and distinct cultivar:

1. Large daisy-type inflorescences that are about 7.7 cm in diameter.
2. Attractive soft pink-colored ray florets and bright yellow-colored disc florets.
3. Very freely flowering with numerous inflorescences per stem.
4. Response time is about 67 days.
5. Dark green foliage.
6. Strong and thick stems.

7. Long peduncles.
8. Good postproduction longevity with inflorescences maintaining good substance and color for at least four weeks in an interior environment.

Plants of the new Chrysanthemum differ from plants of the cultivar Suerte primarily in ray floret color as plants of the cultivar Suerte have dark pink/purple-colored ray florets.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Dusty Pink Suerte' grown as a spray-type cut Chrysanthemum.

The photograph on the second sheet comprises a close-up view of typical inflorescences of 'Dusty Pink Suerte'.

DETAILED BOTANICAL DESCRIPTION

In the following description, color references are made to The Royal Horticultural Society Colour Chart except where general terms of ordinary dictionary significance are used. The following observations and measurements describe plants grown in Madrid, Cundinamarca, Colombia, under conditions which approximate commercial practice in a single-layer polyethlene-covered greenhouse. Two-week old rooted cuttings were planted on Dec. 7, 1999 and received 14 long day/short nights followed by short day/long nights until flowering. Plants were grown as single-stem cut chrysanthemums. During the production time, the following environmental conditons were measured: day temperatures, 19 to 24° C.; night temperatures, 4 to 12° C.; and light levels, 3,000 to 5,000 foot-candles. Measurements and numerical values represent averages for six to ten typical flowering stems.

Botanical classification: *Chrysanthemum×morifolium* cultivar Dusty Pink Suerte.

Commercial classification: Daisy spray-type cut Chrysanthemum.

Parentage: Naturally-occurring whole plant mutation of *Chrysanthemum×morifolium* cultivar Suerte, disclosed in U.S. Plant Pat. No. 10,225.

Propagation:

*Type.*—Terminal tip cuttings.

*Time to rooting.*—About seven to ten days with soil temperatures of 21° C.

*Root description.*—Fine, fibrous and well-branched.

Plant description:

*Appearance.*—Herbaceous daisy spray-type cut flower.

*Flowering stem description.*—Aspect: Erect. Length: About 101.6 cm. Diameter: About 7 mm. Texture: Pubescent. Color: 146A.

*Foliage description.*—Arrangement: Alternate. Length: About 10.4 cm. Width: About 5.6 cm. Apex: Cuspidate. Base: Mostly truncate. Margin: Palmately lobed; sinuses mostly parallel, occasionally convergent or divergent. Texture: Upper and lower surfaces pubescent. Veins prominent on lower surface. Color: Young foliage upper surface: Darker than 147A. Young foliage lower surface: Darker than 147B. Mature foliage upper surface: Darker than 147A; venation, 147B. Mature foliage lower surface: Close to 147B; venation, close to 147B. Petiole: Length: About 2.1 cm. Diameter: About 5 mm. Color: Close to 147B.

Flowering description:

*Appearance.*—Daisy spray-type inflorescence form with elongated oblong-shaped ray florets. Inflorescences borne on terminals, arising from leaf axils. Disc and ray florets arranged acropetally on a capitulum.

*Flowering response.*—Under natural conditions, plants flower in the autumn/winter in the Northern Hermisphere. At other times of the year, inflorescence initiation and development can be induced under short day/long night conditions (at least 13.5 hours of darkness). Plants exposed to two weeks of long day/short night conditions after planting followed by photoinductive short day/long night condtions flower about 67 days later.

*Postproduction longevity.*—In an interior environment, flowering stems will maintain good color and substance for at least four weeks in an interior environment after one week of cool storage.

*Quantity of inflorescences.*—Freely flowering with about 10 inflorescences per flowering stem.

*Inflorescence size.*—Diameter: About 7.7 cm. Depth (height): About 2.9 cm. Diameter of disc: About 1.9 cm. Diameter of receptacle: About 8 mm.

*Ray florets.*—Shape: Elongated oblong. Length: About 4.3 cm. Width: About 1.1 cm. Apex: Mamillate or emarginate. Base: Attenuate. Margin: Entire. Texture: Smooth, satiny, glabrous; longitudinally ridged. Aspect: Initially concave becoming mostly flat with subsequent development. Orientation: Initially upright; when mature, about 60 to 65° from vertical. Number of ray florets per inflorescence: About 93 arranged in about five rows. Color: When opening, upper surface: Initially, 65A to 65B, then close to 69A. When opening, lower surface: Close to 69A to 69B. Mature, upper surface: Close to 69A; fading to 69B with subsequent development. Mature, lower surface: Close to 69A to 69C.

*Disc florets.*—Shape: Tubular, flared at apex. Length: About 8 mm. Width: Apex: About 2.5 mm. Base: About 1 mm. Number of disc florets per inflorescence: Numerous, typically about 134. Color: Immature: 144A. Mature: Apex: 9A. Mid-section: Close to 154A. Base: 155D.

*Peduncle.*—Strength: Strong. Aspect: Angled about 45° from vertical. Length: First peduncle: About 15.6 cm. Fourth peduncle: About 21.6 cm. Seventh peduncle: About 26.1 cm. Diameter: About 3 mm. Texture: Very fine pubescence. Color: 146A.

*Reproductive organs.*—Androecium: Present on disc florets only. Anther color: 9A. Amount of pollen: Scarce to moderate. Color: 14A. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures as high as 40° C.

It is claimed:

1. A new and distinct cultivar of Chrysanthemum plant named 'Dusty Pink Suerte', as illustrated and described.

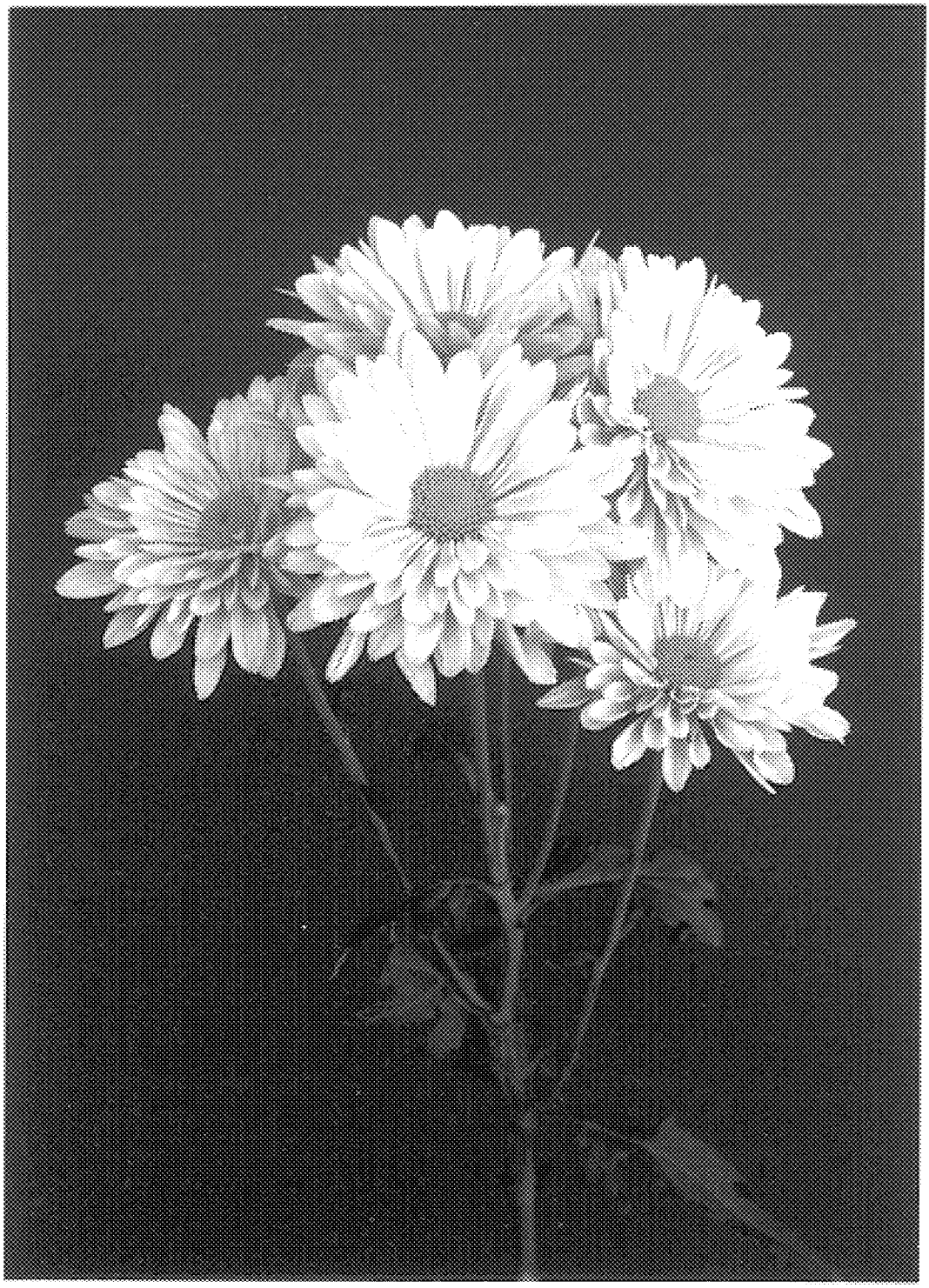

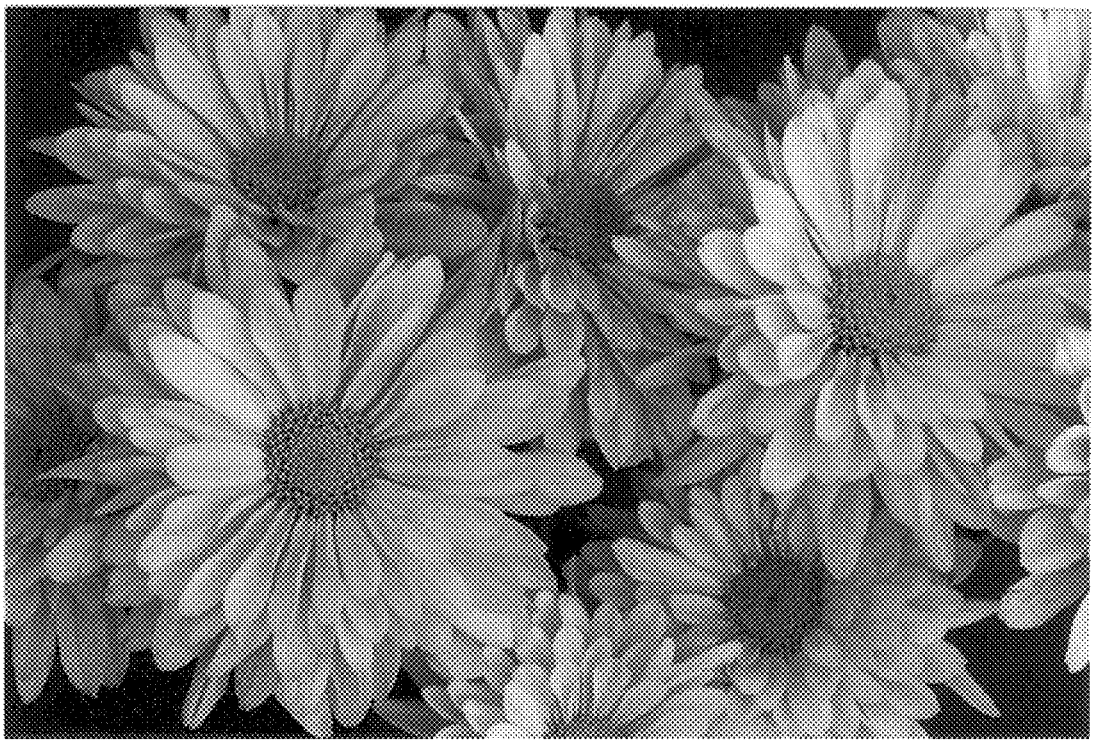

* * * * *